(12) United States Patent
Benner et al.

(10) Patent No.: US 8,541,739 B2
(45) Date of Patent: Sep. 24, 2013

(54) PRECESSION DIFFRACTION CHARGED PARTICLE BEAM SYSTEM

(75) Inventors: Gerd Benner, Aalen (DE); Harald Niebel, Oberkochen (DE)

(73) Assignee: Carl Zeiss Microscopy GmbH, Jena (DE)

( * ) Notice: Subject to any disclaimer, the term of this patent is extended or adjusted under 35 U.S.C. 154(b) by 135 days.

(21) Appl. No.: 13/190,871

(22) Filed: Jul. 26, 2011

(65) Prior Publication Data

US 2012/0025094 A1 Feb. 2, 2012

Related U.S. Application Data

(60) Provisional application No. 61/368,718, filed on Jul. 29, 2010.

(30) Foreign Application Priority Data

Jul. 29, 2010 (EP) .................................... 10007939

(51) Int. Cl.
*G01N 23/20* (2006.01)
*G21K 1/10* (2006.01)

(52) U.S. Cl.
USPC ........................................................ 250/311

(58) Field of Classification Search
USPC .............. 250/310, 311, 306, 396 ML, 396 R
See application file for complete search history.

(56) References Cited

U.S. PATENT DOCUMENTS 2,802,110 A * 8/1957 Ito et al. .................... 250/311
5,013,913 A * 5/1991 Benner ...................... 250/311
(Continued)

FOREIGN PATENT DOCUMENTS

| EP | 0 451 370 | 10/1991 |
| EP | 1 318 539 B1 | 12/2005 |
| EP | 2 068 344 A2 | 6/2009 |
| WO | WO 2005/022582 A1 | 3/2005 |

OTHER PUBLICATIONS

"ASTAR: Automatic Crystal Orientation and Phase Mapping package for TEM" as printed from www.nanomegas.com on Jun. 15, 2010.

(Continued)

*Primary Examiner* — David A Vanore
*Assistant Examiner* — Brooke Purinton
(74) *Attorney, Agent, or Firm* — Fish & Richardson P.C.

(57) ABSTRACT

A charged particle beam system for performing precession diffraction includes a lens 11 for focusing a beam 5 in an object plane 9, and an objective lens 13 having a diffraction plane 27. A doublet 53 of lenses 35, 63 images the diffraction plane 27 into an intermediate diffraction plane 69 where a multipole 55 is located. A doublet 57 of lenses 65, 93 images the intermediate diffraction plane 69 into an intermediate diffraction plane 71 where a multipole 59 is located. A first deflection system 15 upstream of the object plane 9 can tilt to change an angle of incidence of the beam on the object plane. A second deflection system 37 between lenses 35 and 63 tilts the beam such that the change of the angle of incidence of the charged particle beam on the object plane is compensated.

20 Claims, 3 Drawing Sheets

(56) References Cited

U.S. PATENT DOCUMENTS

| | | | |
|---|---|---|---|
| 5,483,073 A * | 1/1996 | Benner | 250/311 |
| 7,223,983 B2 | 5/2007 | Kawasaki et al. | |
| 7,321,124 B2 | 1/2008 | Rose | |
| 7,807,965 B2 | 10/2010 | Zach et al. | |
| 2003/0111613 A1 | 6/2003 | Rose | |
| 2007/0023659 A1 | 2/2007 | Sergeevich et al. | |
| 2007/0284528 A1 * | 12/2007 | Benner et al. | 250/311 |
| 2008/0067378 A1 * | 3/2008 | Kawasaki et al. | 250/310 |
| 2010/0084567 A1 * | 4/2010 | Sawada et al. | 250/396 ML |
| 2011/0049363 A1 * | 3/2011 | Koch | 250/311 |
| 2011/0133084 A1 * | 6/2011 | Nagaoki et al. | 250/311 |
| 2011/0210249 A1 * | 9/2011 | Benner | 250/310 |

OTHER PUBLICATIONS

"Identification—Fingerprinting—Solving ab-into Nanostructures by Precession Electron Diffraction" as printed from www.nanomegas.com on Jun. 15, 2010.

Avilov et al.: "Scanning system for high-energy electron diffractometry", Journal of Applied Crystallography, vol. 32, 1999, pp. 1033-1038.

Vincent et al.: "Double conical beam-rocking system for measurement of integrated electron diffraction intensities", Ultramicroscopy, vol. 53, 1994, pp. 271-282.

Extended European Search Report in European patent application No. 10 007 939.1 dated Mar. 30, 2011.

* cited by examiner

PRECESSION DIFFRACTION CHARGED PARTICLE BEAM SYSTEM

CROSS-REFERENCES TO RELATED APPLICATIONS

The present application claims priority under 35 U.S.C. §119(e)(1) of U.S. Ser. No. 61/368,718, filed on Jul. 29, 2011 in the United States of America, entitled "CHARGED PARTICLE BEAM SYSTEM". The present application also claims priority under 35 U.S.C. §119 of German patent application serial number 10 007 939.1, filed on Jul. 29, 2011 in Europe, entitled "CHARGED PARTICLE BEAM SYSTEM". The contents of these applications are hereby incorporated by reference.

FIELD

The present disclosure relates to a charged particle beam system which can be used to measure diffraction patterns and in which a charged particle beam incident on a sample can be tilted.

BACKGROUND

X-ray diffraction, neutron diffraction and electron diffraction are commonly used to determine crystal structures of samples. Herein, x-ray diffraction is useful in analyzing single crystals of sizes down to some µm, whereas electron beam diffraction can be applied to even smaller crystal sizes since an electron beam probe may have a very low diameter and due to a higher scattering cross section of electrons. The higher scattering cross section of electrons also results in multiple scattering of the electrons in the sample such that both desired single scattering events and undesired multiple scattering events are recorded in a scattering image. A method known as precession diffraction can be used to reduce the amount of multiple scattering events relative to single scattering events in a recorded scattering image such that a crystal structure of a measured sample can be derived from such image with a higher accuracy.

In precession diffraction, a deflection system upstream of a sample in a transmission electron microscope is used to tilt an incident beam such that it rotates about its location of incidence on the sample. A second deflection system downstream of the sample and upstream of a detector compensates the rotating tilt of the incident beam such that a stable diffraction pattern can be recorded on the detector. This recorded diffraction pattern is better suited to derive a crystal structure of the sample than a corresponding pattern recorded without the rotating tilt of the incident beam.

SUMMARY

It is desirable to improve a quality of diffraction patterns obtained with precession diffraction.

The disclosure has been accomplished taking the above problems into consideration.

The disclosure provides a charged particle beam system that allows for recording diffraction patterns at a high accuracy and using a tilted particle beam incident on a sample.

According to embodiments of a charged particle beam system, a charged particle beam system includes a charged particle beam generator, a first lens configured to focus a beam generated by the charged particle beam generator in an object plane, a second lens located downstream of the object plane, a first deflection system upstream of the first lens and configured to tilt the beam about the object plane such that an angle of incidence of the charged particle beam on the object plane is changed, a second deflection system located downstream of the second lens and configured to tilt the beam such that a change of the angle of incidence of the charged particle beam on the object plane generated by the first deflection system is compensated, and a corrector located downstream of the second lens and configured to compensate for imaging errors introduced by the second lens.

According to further embodiments of a charged particle beam system, a charged particle beam system includes a charged particle beam generator, a first lens configured to focus a beam generated by the charged particle beam generator in an object plane, a second lens located downstream of the object plane, a first deflection system upstream of the first lens and configured to tilt the beam about the object plane such that the charged particle beam is obliquely incident on the object plane, a second deflection system located downstream of the second lens and configured to tilt the beam such that a tilt of the charged particle beam generated by the first deflection system is compensated, and a corrector located downstream of the second lens and configured to compensate for imaging errors introduced by the second lens.

Herein, the first deflection system can be configured such that the charged particle beam is obliquely incident on the object plane having an angle of incidence significantly deviating from normal incidence. For example, an angle between a surface normal of the object plane and a direction of a central axis of the charged particle beam incident on the object plane can be greater than 1 mrad, greater than 3 mrad or greater than 10 mrad.

According to embodiments, the corrector includes a first lens doublet located downstream of the second lens, a first multipole located downstream of the first lens doublet, a second lens doublet located downstream of the first multipole and a second multipole located downstream of the second lens doublet. Herein, a multipole is a particle optical component generating a magnetic field and/or an electric field having multipole symmetry about an optical axis of the corrector, wherein the multipole symmetry is higher than dipole symmetry. Examples of such multipole symmetry are a quadrupole symmetry, a hexapole symmetry and an octupole symmetry, and the corresponding particle optical components are a quadrupole, a hexapole and an octupole, respectively.

According to embodiments, the second deflection system and the corrector are integrated in that components of the second deflection system and the corrector overlap along an optical axis of the charged particle beam system. According to particular embodiments herein, at least one deflector of the second deflection system is located between two lenses of the first lens doublet.

According to further embodiments herein, the second deflection system is configured to tilt the beam about a location within a plane located downstream of the second lens and upstream of the first multipole.

According to exemplary embodiments herein, the second deflection system is configured to tilt the beam about a location within an intermediate image plane into which the object plane is imaged by the second and third lenses.

According to further exemplary embodiments herein, the second deflection system includes a first deflector located at the intermediate image plane, wherein, in some embodiments, the second deflection system is free of additional deflectors located outside of the intermediate image plane.

According to an exemplary embodiment, a charged particle beam system includes a charged particle beam generator; a first lens configured to focus a beam generated by the charged particle beam generator in an object plane; a second lens located downstream of the object plane and having a diffraction plane; a first lens doublet located downstream of the second lens and including a third lens and a fourth lens and configured to image the diffraction plane into a first intermediate diffraction plane; a first multipole located at the first intermediate diffraction plane; a second lens doublet located downstream of the first multipole and including a fifth lens and a sixth lens and configured to image the first intermediate diffraction plane into a second intermediate diffraction plane; a second multipole located at the second intermediate diffraction plane; a first deflection system upstream of the first lens and configured to tilt the beam about the object plane such that an angle of incidence of the charged particle beam on the object plane is changed; and a second deflection system located downstream of the third lens and upstream of the fourth lens and configured to tilt the beam such that a change of the angle of incidence of the charged particle beam on the object plane generated by the first deflection system is compensated.

According to exemplary embodiments herein, the second deflection system includes a first deflector located at an intermediate image plane into which the object plane is imaged by the second and third lenses, wherein it is possible that the second deflection system does not include any other deflectors apart from the deflector located at the intermediate image plane.

According to other embodiments herein, the second deflection system includes two or more deflectors which are controlled such that the beam appears to be tilted about a virtual location in the intermediate image plane.

According to some embodiments, the fourth lens and the fifth lens are configured to image the first intermediate image plane into a second intermediate image plane located downstream of the fifth lens and upstream of the sixth lens.

According to further embodiments, the system includes a tilt controller configured to control an amount of beam tilt generated by the first deflection system in synchronism with an amount of beam tilt generated by the second deflection system. With such controller it is possible to generate a tilt of the beam incident on the object plane such that it rotates about an optical axis of the first lens along a cone shaped surface. Downstream of the object plane, this beam tilt is compensated by the second deflection system such that the beam propergates parallel to the optical axis downstream of the second deflection system. This allows recording of diffraction patterns when precession diffraction methods are applied.

According to exemplary embodiments herein, the tilt controller is configured to control the first and second deflection systems such that the amounts of beam tilt generated by the first and second deflection systems change at frequencies greater than 50 Hz or greater than 100 Hz.

According to exemplary embodiments, the charged particle beam system includes a corrector controller configured to control components of the corrector. According to exemplary embodiments herein, the corrector controller is configured to control one or more of the third, fourth, fifth and sixth lenses and the first and second multipoles.

According to particular embodiments herein, the charged particle beam system includes a switch for switching an operation mode of the system from a first mode to a second mode. In the first mode of operation, the second deflection system is controlled by the tilt controller, whereas the second deflection system is controlled by the corrector controller in the second mode of operation. Precession diffraction can be performed in the first mode of operation. If this is not desired, the system can be switched to the second mode in which the second deflection system can be used, under the control of the corrector controller, to adjust the beam relative to an optical axis of the corrector and to improve a performance of the corrector.

According to particular embodiments herein, the corrector controller includes a low-pass filter configured such that control signals supplied to deflectors of the second deflection system are substantially free of signal components having frequencies greater than 30 Hz.

According to exemplary embodiments, the charged particle beam system includes a seventh lens located downstream of the second multipole, wherein the sixth lens and the seventh lens are configured to image the second intermediate image into a third intermediate image. According to an exemplary embodiment herein, the sixth lens and the seventh lens are further configured to generate a virtual image of the diffraction plane.

According to exemplary embodiments, the charged particle system includes an energy filter having an entrance pupil plane and an entrance image plane, wherein the energy filter is located downstream of the corrector.

The energy filter provides a dispersion to charged particles traversing the energy filter and is configured such that the entrance image plane of the energy filter is achromatically imaged by the energy filter into an exit image plane of the energy filter located at an exit side of the energy filter or downstream of the energy filter. The entrance pupil plane of the energy filter is dispersively imaged by the energy filter into an exit pupil plane of the energy filter located at the exit side of the energy filter or downstream of the energy filter. With such configuration it is possible to use a slit shaped aperture located in the exit pupil plane of the energy filter to restrict an energy spread of the charged particles contributing to the imaging downstream of the energy filter without disturbing the imaging of a plane imaged into the entrance image plane of the energy filter.

According to embodiments herein, an eight lens is located upstream of the energy filter and configured such that an image or intermediate image of the object plane is generated at the entrance pupil plane of the energy filter and/or such that an image or intermediate image of the diffraction plane of the second lens is imaged into the entrance image plane of the energy filter.

According to exemplary embodiments, a slit shaped aperture is arranged in the exit pupil plane of the energy filter such that only so called "zero loss charged particles" can traverse the energy filter. In such configuration only charged particles which have been elastically scattered at the object can traverse the energy filter, whereas charged particles which have been inelastically scattered at the object and have experienced a loss of kinetic energy are prevented from traversing the energy filter. This may have an advantage in that an image blurring of the recorded diffraction image is significantly reduced, such that a contrast in the recorded diffraction image is increased. This provides advantages to ensure that also diffraction maxima of low intensities can contribute an analysis of the diffraction patterns contained in a recorded image.

According to some embodiments, the first deflection system is further configured to displace the beam in the object plane such that a location of incidence of the beam on the object plane is changed. Thus, the first deflection system is configured to change both the angle of incidence of the beam on the object plane and the location of incidence of the beam in the object plane. The beam can be selectively directed to plural locations of interest within the sample, and precession diffraction can be performed at each such location of interest.

In exemplary embodiments herein, the charged particle beam system includes a third deflection system located downstream of the corrector and configured to tilt the beam such that a change of the locations of incidence of the charged particle beam on the object plane generated by the first deflection system is compensated.

In embodiments using the energy filter, the third deflection system may be configured to tilt the beam about the entrance image plane of the energy filter into which the diffraction plane of the objective lens is imaged. According to embodiments herein, the third deflection system may include a single deflector located in the entrance image plane of the energy filter or two or more deflectors located upstream of the entrance image plane of the energy filter and controlled such that the beam is tilted about a virtual location positioned in the entrance image plane of the energy filter, such that the off-axis beam is shifted back to the optical axis.

According to embodiments, the charged particle beam system includes a displacement controller configured to control an amount of beam displacement generated by the first deflection system in synchronism with an amount of beam tilt generated by the third deflection system.

According to embodiments, one or more or all of the deflection systems mentioned above are configured to deflect the charged particle beam in two independent directions, such as orthogonal x- and y-directions. For this purpose, the deflector or the two deflectors of the deflection system may include two pairs of deflection elements distributed about the optical axis of the charged particle system. For example, the pairs of deflection elements may include pairs of electrodes for providing deflecting electrical fields and/or pairs of coils providing deflecting magnetic fields. The pairs of deflection elements may be energised such that one pair is energised according a signal having a temporal shape following a cosine function while the other pair is energised according a signal having a temporal shape following a sine function. If the first deflection system is energised according to such pattern, the charged particle beam obliquely incident on the object plane will perform a precession about the optical axis of the charged particle system.

BRIEF DESCRIPTION OF THE DRAWINGS

The forgoing as well as other advantageous features of the disclosure will be more apparent from the following detailed description of exemplary embodiments of the disclosure with reference to the accompanying drawings. It is noted that not all possible embodiments of the present disclosure necessarily exhibit each and every, or any, of the advantages identified herein.

DETAILED DESCRIPTION OF EXEMPLARY EMBODIMENTS

In the exemplary embodiments described below, components that are alike in function and structure are designated as far as possible by alike reference numerals. Therefore, to understand the features of the individual components of a specific embodiment, the descriptions of other embodiments and of the summary of the disclosure should be referred to.

Figure 1:
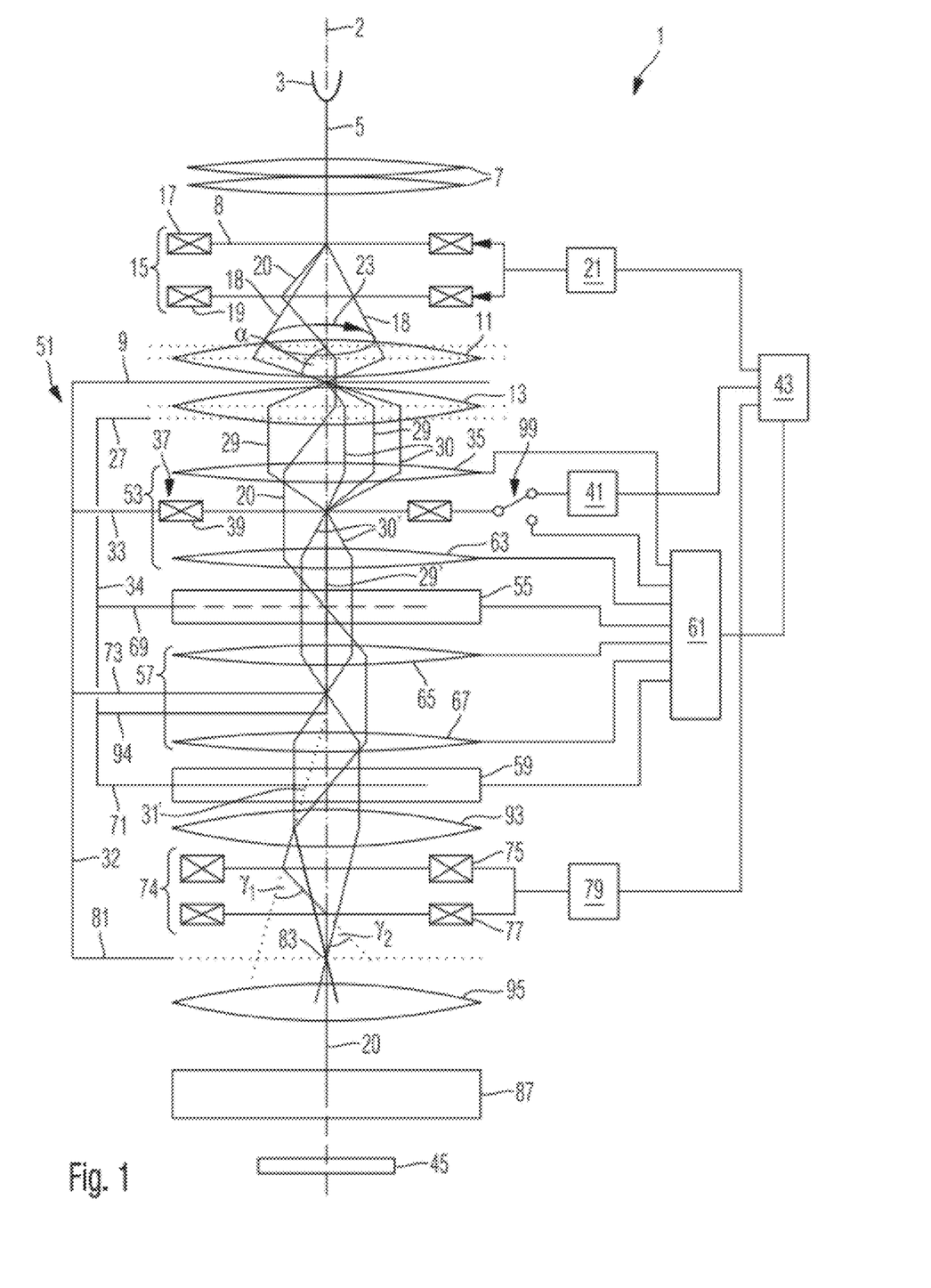
FIG. 1 is a schematic illustration of a charged particle beam system allowing to perform precession diffraction.

FIG. 1 is a schematic illustration of a charged particle beam system 1 having a configuration of a transmission electron microscope. The charged particle beam system 1 includes a charged particle beam generator 3 configured to generate a charged particle beam 5. In the illustrated embodiment, the charged particle beam generator is an electron source, such that the charged particle beam 5 is an electron beam. However, other sources of charged particles, such as ions, are envisaged within the scope of the present disclosure.

The charged particle beam 5 is collimated by one or more lenses 7 to shape the beam 5 such that it has a small cross section and a low convergence in a plane 8. For example, the cross section of the beam 5 can be smaller than 50 μm and the convergence of the beam 5 can be smaller than 1.5 mrad in the plane 8. The plane 8 is imaged into an object plane 9 by a lens 11. A sample to be inspected can be positioned in the object plane 9. A second lens 13 is located downstream of the object plane 9 and forms the objective lens of the transmission electron microscope. In the illustration of FIG. 1, the lenses 11 and 13 are represented as two individual lenses for illustrative purposes. It is also possible to provide the functions of the two lenses 11 and 13 by one single lens configuration which is referred to as condenser-objective-single-field-lens according to Riecke-Ruska. Similarly, some groups of other individual lenses shown in the illustration of FIG. 1 can be embodied in practice by one single lens structure while it is also possible that some of the individual single lenses shown in the illustration in FIG. 1 are embodied in practice by groups of plural lens structures.

A first deflection system 15 is provided upstream of the first lens in the beam path of the charged particle beam 5. The first deflection system 15 includes two deflectors 17 and 19 spaced apart along an optical axis 2 of the first lens 11. In the illustrated example, the deflector 17 is located in the plane 8 where the beam spot is formed by the lens 7. The deflectors 17 and 19 are controlled by a deflector controller 21 which is configured to independently perform two functions of tilting the beam about the object plane 9 and displacing the beam in the object plane 9. Reference numerals 18 in FIG. 1 illustrate beams which are deflected by the deflection system 15 such that a location of incidence on the object plane of the beam 5 is on the optical axis 2, while the beam 5 is tilted relative to the optical axis 2 by angles +α and −α, respectively, wherein α is greater than 0. In exemplary embodiments, α may have values from 3 mrad to 100 mrad, for example. Moreover, the controller 21 is configured such that the direction of incidence of the beam can be rotated about the optical axis 2 while maintaining the angle α constant as illustrated by an arrow 23 in FIG. 1. Reference numeral 20 in FIG. 1 illustrates a beam which is deflected by the deflection system 15 such that the location of incidence of the beam is displaced within the object plane 9, wherein the tilt angle α is 0. The controller is configured to energize the deflection system 15 such that both a location of incidence of the beam 5 in the object plane 9 and a tilt angle α relative to the optical axis 2 can be independently adjusted.

The second lens 13 has a focal plane 27 located downstream of the object plane 9. Reference numeral 29 in FIG. 1 illustrates a charged particle ray which was tilted relative to the optical axis 2 by an angle α, which traversed the object plane on the optical axis 2 (axial ray) and which has not been scattered by the object. Reference numerals 30 in FIG. 1 illustrate charged particle rays which were tilted relative to the optical axis 2 by the angle α and which have been scattered by the object by a scattering angle towards the optical axis and away from the optical axis, respectively.

An intermediate image of the object plane 9 is generated in an intermediate image plane 33 located downstream of the lens 13. In the illustrated example, the intermediate image in the intermediate image plane 33 is generated by the second lens 13 and an additional lens 35. According to other examples, it is possible that the additional lens 35 is omitted and that the intermediate image is generated directly by the lens 13.

Lines 32 in FIG. 1 connect, for illustrative purposes, planes which are conjugate to each other and conjugate to the object plane 9, while lines 34 connect planes which are conjugate to each other and conjugate to the focal plane 27 of objective lens 13.

A second deflection system 37 is located downstream of the lens 13 and configured to tilt the beam about a location in the intermediate image plane 33. In the illustrated example, the second deflection system 37 includes one single deflector 39 positioned in the intermediate image plane 33. According to other examples, the second deflection system 37 may include plural deflectors configured such that the beam can be tilted about a (virtual) location in the intermediate image plane 33.

The second deflection system 37 is controlled by a controller 41 configured to adjust a deflection angle or tilt generated by the second deflection system 37. The controller 41 of the second deflection system 37 and the controller 21 of the first deflection system 15 are controlled by a main controller 43 such that a beam tilt generated by the first deflection system 15 upstream of the object plane 9 is compensated by a tilt generated by the second deflection system 37 downstream of the object plane 9. This has an effect that the tilted rotating beam upstream of the second deflection system 37 which is illustrated by a ray 29, and a bundle of scattered rays 30 are deflected by the second deflection system 37 such that they travel symmetrically to the optical axis 2 downstream of the second deflection system 37 as indicated by reference numerals 29' and 30' in FIG. 1. A stationary diffraction pattern is formed by these rays in the intermediate diffraction plane 69 as illustrated in more detail below.

The beam traversing the sample positioned in the object plane 9 is diffracted by the sample, and a corresponding diffraction pattern can be recorded by a detector 45 positioned downstream of the object plane 9.

Figure 2A:
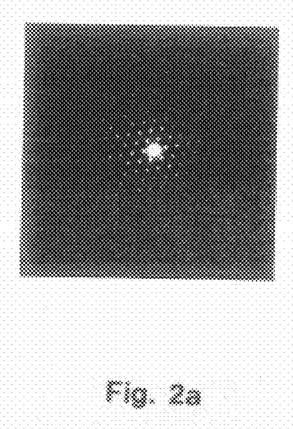
FIG. 2 shows exemplary diffraction patterns for illustrating advantages of precession diffraction.

FIG. 2a shows an exemplary diffraction pattern recorded with a non-tilted beam from a sample including an uvarovite crystal.

Figure 2B:
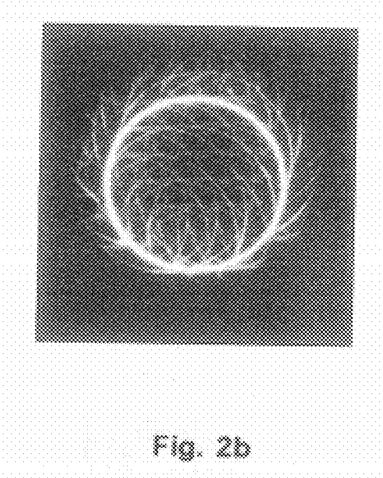

FIG. 2b shows a diffraction pattern obtained when the incident beam is tilted and rotated about the optical axis by the first deflection system 15 while the second deflection system 37 is not operated to compensate for the tilt and rotation.

Figure 2C:
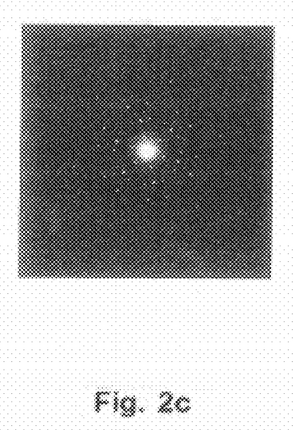

FIG. 2c is an illustration of a diffraction pattern recorded from a tilted rotating beam wherein the second deflection system 37 is operated as illustrated above to compensate the beam tilt and rotation. It is evident that the diffraction pattern of FIG. 2c shows less dynamical scattering than the diffraction pattern of FIG. 2a which makes it better suitable for deriving a crystal structure of the sample.

Figure 2D:
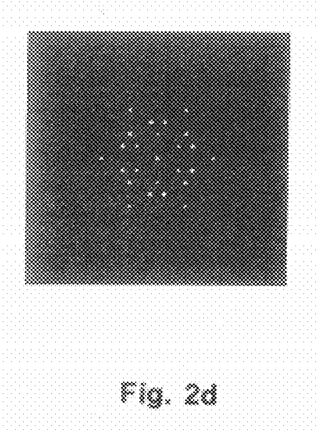

FIG. 2d shows a diffraction pattern derived from the uvarovite crystal structure by calculation and simulation. The diffraction pattern of FIG. 2c has a higher similarity with the expected pattern of FIG. 2d than the pattern of FIG. 2a which is obtained without precession diffraction. It is apparent that precession diffraction is helpful in obtaining diffraction patterns allowing to derive complicated crystal structures of measured samples.

The charged particle beam system 1 illustrated in FIG. 1 includes a corrector 51 located downstream of the objective lens 13 and upstream of the detector 45 and configured to compensate aberrations generated by the objective lens 13. In the illustrated example, the corrector 51 includes a lens 53, a hexapole 55, a lens 57 and a hexapole 59 arranged in that order along the optical axis 2. As illustrated in FIG. 1, the lens 53 can be formed by a lens doublet of lenses 35 and 63, and also the lens 57 can be formed of a lens doublet of lenses 65 and 67. While the corrector of the illustrated example includes hexapoles as multipole elements, other examples of correctors include other types of multipoles, such as quadrupoles and octupoles. Background information relating to correctors of various types can be obtained from U.S. Pat. No. 7,223,983 B2, EP 0 451 370 A1 and U.S. Pat. No. 7,321,124 B2, wherein the full disclosure of these documents is incorporated herein by reference.

The components of the corrector 51 are controlled by a corrector controller 61 such that the diffraction plane 27 of lens 13 is imaged into an intermediate diffraction plane 69 at which the first hexapole 55 is located. Further, the lens 57 images the intermediate diffraction plane 69 into a further intermediate diffraction plane 71 at which the second hexapole 59 is located. Still further, the intermediate image plane 33 may be imaged into a further intermediate image plane 73 located between the hexapole 55 and the hexapole 59. In the illustrated example, the further intermediate image plane 73 is located in between lenses 65 and 67 of the lens doublet 57.

The corrector 51 is controlled by the controller 61 such that lens aberrations, such as a spherical aberration of the objective lens 13 and possibly other aberrations are reduced or compensated. In the illustrated example, the two hexapoles 55 and 59 provide, in cooperation, an effect of a negative aberration coefficient which is suitable to compensate spherical aberrations of the objective lens 13. The present disclosure is, however, not limited to this type of corrector. Other types of correctors are envisaged within the scope of the present disclosure, wherein a deflection system generates a beam tilt at an intermediate image plane located between components of the corrector. In the illustrated example, it is the intermediate image plane 33 about which the second deflection system 37 is capable to tilt the beam for compensating a beam tilt introduced by the first deflection system 15, and wherein the intermediate image plane 33 is located between lenses 35 and 63 of the corrector 51.

A third deflection system 74 is located downstream of the corrector 51 and configured to deflect the beam such that a change of the location of incidence of the charged particle beam 5 on the object plane 9 generated by the first deflection system 15 is compensated. In the illustrated example, the third deflection system 74 includes two deflectors 75, 77 spaced apart along the optical axis 2 and controlled by a controller 79.

As illustrated in the example shown in FIG. 1, the corrector 51 may include an adaptation lens 93, and the charged particle system may further include a projection lens 95. In the illustrated example, the adaptation lens 93 is configured to generate an image of the object plane 9 in an entrance image plane 81 of the projection lens 95. At the same time, the adaptation lens 93 produces a virtual image of the intermediate image 71 of the focal plane 27 at a plane 94. The virtual image plane 94 is located upstream of the lens 95. The virtual image plane 94 can be located upstream of the hexapole 59 as illustrated in the example shown in FIG. 1. Still further, the deflectors 75, 77 of the third deflection system 74 are located in between the adaptation lens 93 and the projection lens 95.

The controller 79 is configured to control the deflectors 75, 77 of the third deflection system 74 such that the beam is tilted about a location in the virtual image plane 94. In the illustrated example, the deflectors 75 and 77 deflect the beam in opposite directions by angles γ1 and γ2, respectively, and such that the field ray 20 displaced by the first deflection system 15 and traversing the sample in the object plane 9 coincides with the optical axis 2 downstream of the deflection system 74, and such that the beam appears to be tilted about location 94 on the optical axis 2.

According to other examples, the third deflection system 73 may include one single deflector which is positioned in any one of the intermediate image planes of the focal plane 27.

The controller 79 of the third deflection system 74 is controlled by the main controller 43 in synchronism with the controller 21 of the first deflection system 15 such that the change of location of incidence of the charged particle beam on the object plane 9 generated by the first deflection system 15 is compensated.

The charged particle system 1 further includes an energy filter 87 located downstream of the corrector 51. As shown in the example illustrated in FIG. 1, the energy filter is located downstream of the projection lens 95. The energy filter 87 has an entrance pupil plane (not shown in FIG. 1) and an entrance image plane (not shown in FIG. 1), and projection lens 95 is configured such that an intermediate image of the object plane 9 is generated in the entrance pupil plane of the energy filter, and that an image of the focal plane 27 of the objective lens 13 is generated in the entrance image plane of the energy filter 87. The lens 95 includes plural individual lenses which are represented in FIG. 1 as one single lens 95. Lens 93 is configured such that an intermediate image of the object plane 9 is generated in the plane 81 located between lenses 93 and 95 by imaging intermediate image plane 73 into intermediate image plane 81. The adaptation lens 93 also generates the virtual image of the focal plane 27 of the second lens 13 in the intermediate image plane 94 as indicated by a broken line 31' in FIG. 1.

The charged particle beam system 1 shown in FIG. 1 can be operated in two modes. In a first mode of operation, the controller 41 of the second deflection system 37 is controlled by the main controller 43 which has a tilt control function for controlling the second deflection system 37 in synchronism with the first deflection system 15 such that a beam tilt and rotation generated by the first deflection system 15 is compensated by the second deflection system 37. In a second mode of operation, the second deflection system 37 is under the control of the corrector controller 61 such that the second deflection system 37 can be used to adjust the corrector 51 and improve its performance. FIG. 1 shows a switch 99 which can be used to change the operation modes of the charged particle beam system 1 by connecting the second deflection system 37 to one of the deflection controller 41 to perform the tilt control function and the corrector controller 61 controlling the corrector 51. The corrector controller 61 includes a low-pass filter in the control path towards the second deflection system 37 such that control signals supplied to the deflectors of the second deflection system 37 are substantially free of signal components having frequencies greater than 30 Hz. This allows for a stable operation of the corrector 51. On the other hand, the deflection controller 41 performing the tilt compensation function is configured to control the controller 41 of the second deflection system 37 such that it can generate beam deflections at frequencies greater than 50 Hz.

In both the first and second operation modes of the charged particle beam system 1, the main controller 43 can perform its deflection control function to control the controller 79 of the third deflection system 74 such that a deflection of the location of incidence of the beam in the object plane 9 generated by the first deflection system 15 is compensated.

Figure 3:
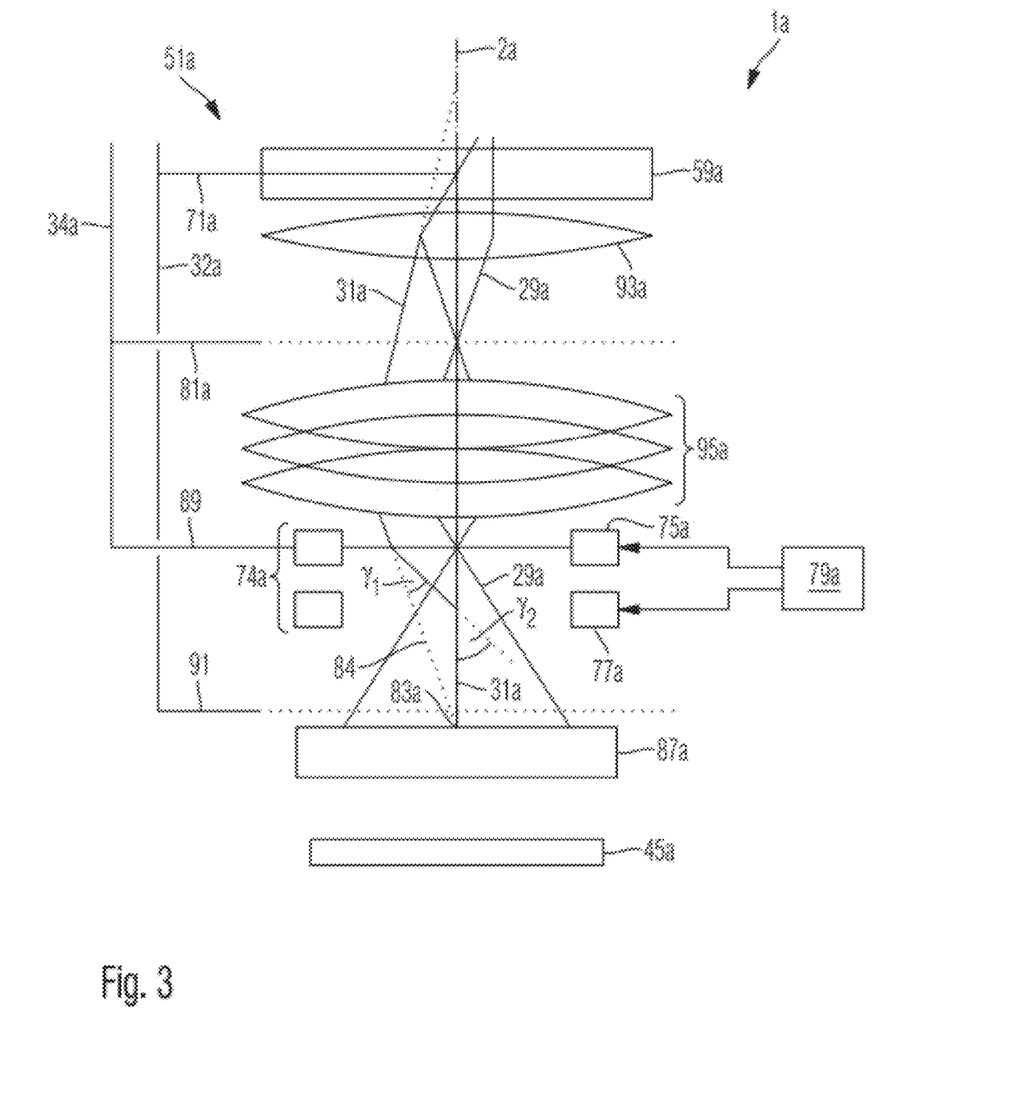
FIG. 3 is a schematic illustration of apportion of a further charged particle beam system allowing to perform precession diffraction.

FIG. 3 shows a portion of a further example of a charged particle beam system which is a variation of the system illustrated with reference to FIG. 1 above. The charged particle beam system 1a shown in FIG. 3 has a charged particle beam generator, lenses, first and second deflection systems for performing precession diffraction similar to the system illustrated with reference to FIG. 1 and not shown in FIG. 3. The system 1a also includes a corrector having two hexapoles and lenses similar to the corrector of the system illustrated with reference to FIG. 1, wherein only a hexapole 59a and a lens 93a of the corrector 51a are shown in FIG. 3. The system 1a differs from the one illustrated with reference to FIG. 1 above in that a projection lens 95a is located downstream of the lens 93a of the corrector 51a and upstream of a third deflection system 74a, wherein the third deflection system 74a is located upstream of an energy filter 87a.

The third deflection system 74a is configured to deflect the beam such that a change of the location of incidence of the charged particle beam on an object plane of the system generated by the first deflection system is compensated. In the illustrated example, the third deflection system 74a includes two deflectors 75a, 77a spaced apart along an optical axis 2a. The deflectors 75a, 77a of the third deflection system 74a are controlled by a controller 79a to tilt the beam about a location in a plane 91a at which an intermediate image of a focal plane of an objective lens of the system is formed. In the illustrated example, the deflectors 75a and 77a deflect the beam in opposite directions by angles γ1 and γ2, respectively and such that a field ray 31a originating from the object plane coincides with the optical axis 2a and such that the beam appears to be tilted about location 83a on the optical axis 2a and in the intermediate image plane 81a as indicated by a broken line 84. According to other examples, the third deflection system 73a may include one single deflector which is positioned in the intermediate image plane 81a.

The controller 79a of the third deflection system 73 is controlled by a main controller (not shown in FIG. 1) of the system in synchronism with the first deflection system such that the change of location of incidence of the charged particle beam on the object plane generated by the first deflection system is compensated.

The energy filter 87a is located downstream of the corrector 51a. The energy filter 87a has an entrance pupil plane 89a and an entrance image plane 91. Lenses 93a and 95a are located between the corrector 51a and the entrance pupil plane 89 and entrance image plane 91 of the energy filter 87 and configured such that an intermediate image of the object plane is generated in the entrance pupil plane 89a of the energy filter, and such that an image of the focal plane of the objective lens is generated in the entrance image plane 91 of the energy filter 87. The lens 95a includes plural individual lenses as represented in FIG. 1. The lens 93a is configured such that an intermediate image of the object plane is generated in an intermediate image plane 97a located between the lenses 93a and 95a.

The lens 93a also generates a virtual image of the focal plane of the objective lens upstream of the lens 93a.

The present disclosure illustrates certain exemplary embodiments wherein it is evident that many alternatives, modifications and variations will be apparent to those skilled in the art. Therefore, the exemplary embodiments illustrated in this disclosure are intended to be illustrative and not limiting in any way. Various changes may be made without departing from the spirit and scope of the present disclosure as defined in the following claims.

What is claimed is:

1. A charged particle beam system, comprising:
   a charged particle beam generator configured to generate a charged particle beam having a beam path;
   a first lens configured to focus the charged particle beam generated in an object plane;
   a second lens located downstream of the object plane along the beam path, the second lens having a diffraction plane;
   a first lens doublet located downstream of the second lens along the beam path, the first lens doublet comprising a third lens and a fourth lens, the first lens doublet being configured to image the diffraction plane into a first intermediate diffraction plane;
   a first multipole located at the first intermediate diffraction plane;
   a second lens doublet located downstream of the first multipole along the beam path, the second lens doublet comprising a fifth lens and a sixth lens, the second lens doublet being configured to image the first intermediate diffraction plane into a second intermediate diffraction plane;
   a second multipole located at the second intermediate diffraction plane;
   a first deflection system upstream of the object plane along the beam path, the first deflection system being configured to tilt the charged particle beam about the object plane so that the charged particle beam is obliquely incident on the object plane; and
   a second deflection system located downstream of the third lens along the beam path and upstream of the fourth lens along the beam path, the second deflection system being configured to tilt the charged particle beam to compensate for tilting of the charged particle beam due to the first deflection system.

2. The charged particle beam system according to claim 1, wherein the second and third lenses are configured to image the object plane into an intermediate image plane located downstream of the third lens along the beam path and upstream of the fourth lens along the beam path.

3. The charged particle beam system according to claim 2, wherein the second deflection system is configured to tilt the beam about the intermediate image plane.

4. The charged particle beam system according to claim 2, wherein the fourth and fifth lenses are configured to image the first intermediate image plane into a second intermediate image plane located downstream of the fifth lens along the beam path and upstream of the sixth lens along the beam path.

5. The charged particle beam system according to claim 1, further comprising a tilt controller configured to synchronously control an amount by which the charged particle beam tilts due to the first deflection system and an amount by which the charged particle beam tilts due to the second deflection system.

6. The charged particle beam system according to claim 5, wherein the tilt controller is configured to control the first and second deflection systems so that the amounts of beam tilt generated by the first and second deflection systems change at a frequency greater than 50 Hz.

7. The charged particle beam system according to claim 5, wherein the tilt controller is configured to control the first and second deflection systems so that the amounts of beam tilt generated by the first and second deflection systems change at a frequency greater than 100 Hz.

8. The charged particle beam system according to claim 5, further comprising a corrector controller configured to control at least one element selected from the group consisting of the third lens, the fourth lens, the fifth lens, the sixth lens, the first multipole and the second multipole, wherein the corrector controller comprises a low pass filter configured to control the second deflection system.

9. The charged particle beam system according to claim 8, wherein the low pass filter is configured so that control signals supplied to deflectors of the second deflection system are substantially free of signal components having frequencies greater than 30 Hz.

10. The charged particle beam system according to claim 8, further comprising a switch configured to selectively connect the second deflection system to a member selected from the group consisting of the tilt controller and the corrector controller.

11. The charged particle beam system according to claim 1, further comprising an energy filter located downstream of the seventh lens along the beam path, wherein the energy filter has an entrance pupil plane and an entrance image plane.

12. The charged particle beam system according to claim 11, further comprising an eighth lens located upstream of the energy filter along the beam path, wherein the eighth lens is configured to image the object plane or an intermediate image of the object plane into the entrance pupil plane of the energy filter, and/or wherein the eighth lens is configured to image the diffraction plane or an intermediate image of the diffraction plane into the entrance image plane of the energy filter.

13. The charged particle beam system according to claim 11, wherein:
   the first deflection system is configured to displace the charged particle beam in the object plane such that a location of incidence of the charged particle beam on the object plane is changed;
   the charged particle beam system further comprises a third deflection system located upstream of the energy filter along the beam path; and
   the third deflection system is configured to deflect the charged particle beam to compensate a change of the location of incidence of the charged particle beam on the object plane generated by the first deflection system.

14. The charged particle beam system according to claim 13, wherein the third deflection system is located upstream of the eighth lens along the beam path, and the third deflection system is configured to tilt the beam about the entrance image plane of the eighth lens.

15. The charged particle beam system according to claim 13, wherein the third deflection system is located downstream of the eighth lens along the beam path and upstream of the energy filter along the beam path, and the third deflection system is configured to tilt the beam about the entrance image plane of the energy filter.

16. The charged particle beam system according to claim 13, further comprising a displacement controller configured to synchronously control an amount by which the charged particle beam tilts due to the first deflection system and an amount by which the charged particle beam tilts due to the second deflection system.

17. The charged particle beam system of claim 1, wherein the charged particle beam generator is configured to generate an electron beam.

18. The charged particle beam system of claim 1, wherein the charged particle beam generator is configured to generate an ion beam.

19. A charged particle system, comprising:
a charged particle beam generator configured to generate a charged particle beam having a beam path;
a first lens configured to focus the charged particle beam generated in an object plane;
a second lens located downstream of the object plane along the beam path, the second lens having a diffraction plane;
a first lens doublet located downstream of the second lens along the beam path, the first lens doublet comprising a third lens and a fourth lens, the first lens doublet being configured to image the diffraction plane into a first intermediate diffraction plane;
a first multipole located at the first intermediate diffraction plane; a second lens doublet located downstream of the first multipole along the beam path, the second lens doublet comprising a fifth lens and a sixth lens, the second lens doublet being configured to image the first intermediate diffraction plane into a second intermediate diffraction plane;
a second multipole located at the second intermediate diffraction plane;
a first deflection system upstream of the object plane along the beam path, the first deflection system being configured to tilt the charged particle beam about the object plane so that the charged particle beam is obliquely incident on the object plane;
a second deflection system located downstream of the third lens along the beam path and upstream of the fourth lens along the beam path, the second deflection system being configured to tilt the charged particle beam to compensate for tilting of the charged particle beam due to the first deflection system;
a tilt controller configured to synchronously control an amount by which the charged particle beam tilts due to the first deflection system and an amount by which the charged particle beam tilts due to the second deflection system; and
a corrector controller comprising a low pass filter configured to control the second deflection system,
wherein:
the second and third lenses are configured to image the object plane into an intermediate image plane located downstream of the third lens along the beam path and upstream of the fourth lens along the beam path;
the second deflection system is configured to tilt the beam about the intermediate image plane;
the fourth and fifth lenses are configured to image the first intermediate image plane into a second intermediate image plane located downstream of the fifth lens along the beam path and upstream of the sixth lens along the beam path; and
the corrector controller is configured to control at least one element selected from the group consisting of the third lens, the fourth lens, the fifth lens, the sixth lens, the first multipole and the second multipole.

20. A method, comprising:
using the charged particle beam according to claim 1 to obtain a diffraction pattern of a sample.

* * * * *